United States Patent [19]

Ohlson

[11] 4,127,775
[45] Nov. 28, 1978

[54] X-RAY UNIT STAND HAVING FIELD CONTROLLED BRAKE RELEASE

[75] Inventor: Carl-Eric Ohlson, Solna, Sweden

[73] Assignee: AO:s Metall & Mek. Verkstad AB, Stockholm, Sweden

[21] Appl. No.: 765,052

[22] Filed: Feb. 2, 1977

Related U.S. Application Data

[63] Continuation-in-part of Ser. No. 634,056, Nov. 21, 1975, abandoned.

[30] Foreign Application Priority Data

Nov. 25, 1974 [SE] Sweden .............................. 74/14800

[51] Int. Cl.² .......................................... G01N 21/00
[52] U.S. Cl. ................................ 250/490; 250/445 R; 250/525
[58] Field of Search ............... 250/449, 448, 525, 523, 250/445 X, 451, 456

[56] References Cited

U.S. PATENT DOCUMENTS

| | | | |
|---|---|---|---|
| 2,997,591 | 8/1961 | Guentner et al. | 250/525 |
| 3,121,793 | 2/1964 | Thomas | 250/525 |
| 3,215,835 | 11/1965 | Mueller | 250/449 |
| 3,790,805 | 2/1974 | Foderaro | 250/525 |
| 3,866,048 | 2/1975 | Gieschen et al. | 250/449 |

Primary Examiner—Alfred E. Smith
Assistant Examiner—R. L. Anderson
Attorney, Agent, or Firm—Fleit & Jacobson

[57] ABSTRACT

A counter-balanced radiography unit stand comprises a column on which a wing arm bearing the radiography equipment is mounted for vertical displacement and rotary movement. Automatically applied brakes for stopping the vertical displacement and the rotary movement, respectively, are electromagnetically releasable by electrically controlled actuating devices, which when approached or contacted by, for example, the hand of an operator, release the corresponding brake so that the swing arm can be rotated and/or displaced. At least one actuating device for releasing the rotary movement brake and/or the vertical displacement brake is so disposed along a substantial part of the swing arm length, that easy reach of the device is accomplished by a person positioned anywhere in the region of the swing arm.

The said actuating device may comprise at least one handle disposed on the swing arm. In addition external parts of the swing arm may have a blocking element of adjustable sensitivity adapted to control a superimposed blocking function so that the release circuits for the brakes are disconnected when the swing arm approaches or strikes against a person or an object.

5 Claims, 9 Drawing Figures

X-RAY UNIT STAND HAVING FIELD CONTROLLED BRAKE RELEASE

BACKGROUND OF THE INVENTION

This application is a continuation-in-part of Ser. No. 634,056, filed on Nov. 21, 1975 now abandoned.

This invention relates to an arrangement in a counterbalanced radiography or X-ray unit stand, comprising a column on which a swing arm is mounted for vertical displacement and pivotal or rotary movement, said swing arm bearing the radiography equipment. At least one automatically applied brake for preventing the vertical displacement, and at least one automatically applied brake for preventing the rotary movement is provided. The brakes are electromagnetically releasable by a solenoid when an electrically controlled actuating device is approached, or contacted, by the hand of an operator. After the corresponding brake is released, the swing arm can be rotated and/or displaced.

Swedish patent specifications Nos. 147,338 and 201,217 show different examples of previously known radiography unit stands.

SUMMARY OF THE INVENTION

One of the objects of the invention is to provide an improved radiography unit stand of the above kind, which is easier to handle and operate for the operators and which also has increased safety features so that the risk of injury to persons or damage to objects in the vicinity of the stand during its actuation, or to the stand itself due to contact with objects in its vicinity, can be appreciably reduced.

The operators then have the maximum freedom of choice in carrying out positional adjustments. When the swing arm has to be adjusted into positions of difficult access, it is possible to carry out an adjustment regardless of where the operator is positioned along the swing arm or whatever body position the operator has to assume to be able to carry out the adjustment.

Since the position of the swing arm can be adjusted only by touching the actuating device, it is impossible for the swing arm to be displaced or swung so uncontrollably as to entail the risk of damage to the swing arm or injury to persons or injury to object in its area.

In practice, the actuating device is preferably embodied as a handle disposed along the column arm or swing arm.

Preferably, two longitudinal handles extend along a substantial part of the entire length of the swing arm, one being adapted to release the pivotal or rotary movement brake, and the other to release the vertical displacement brake. As an alternative, a number of handles of shorter length can be distributed over the swing arm.

The swing arm can, thus, be displaced to the required height by holding one handle, which releases the vertical brake, for example, and after vertical displacement, the desired pivoting angle can be obtained by holding the other handle which releases the rotary brake.

In addition to the actuating device handles, external parts of the swing arm also have a blocking element of adjustable sensitivity to provide a superimposed blocking function so that the release circuits for the brakes are disconnected or disabled when the swing arm approaches or strikes against a person or object.

DETAILED DESCRIPTION OF THE DRAWINGS

Figure 1:
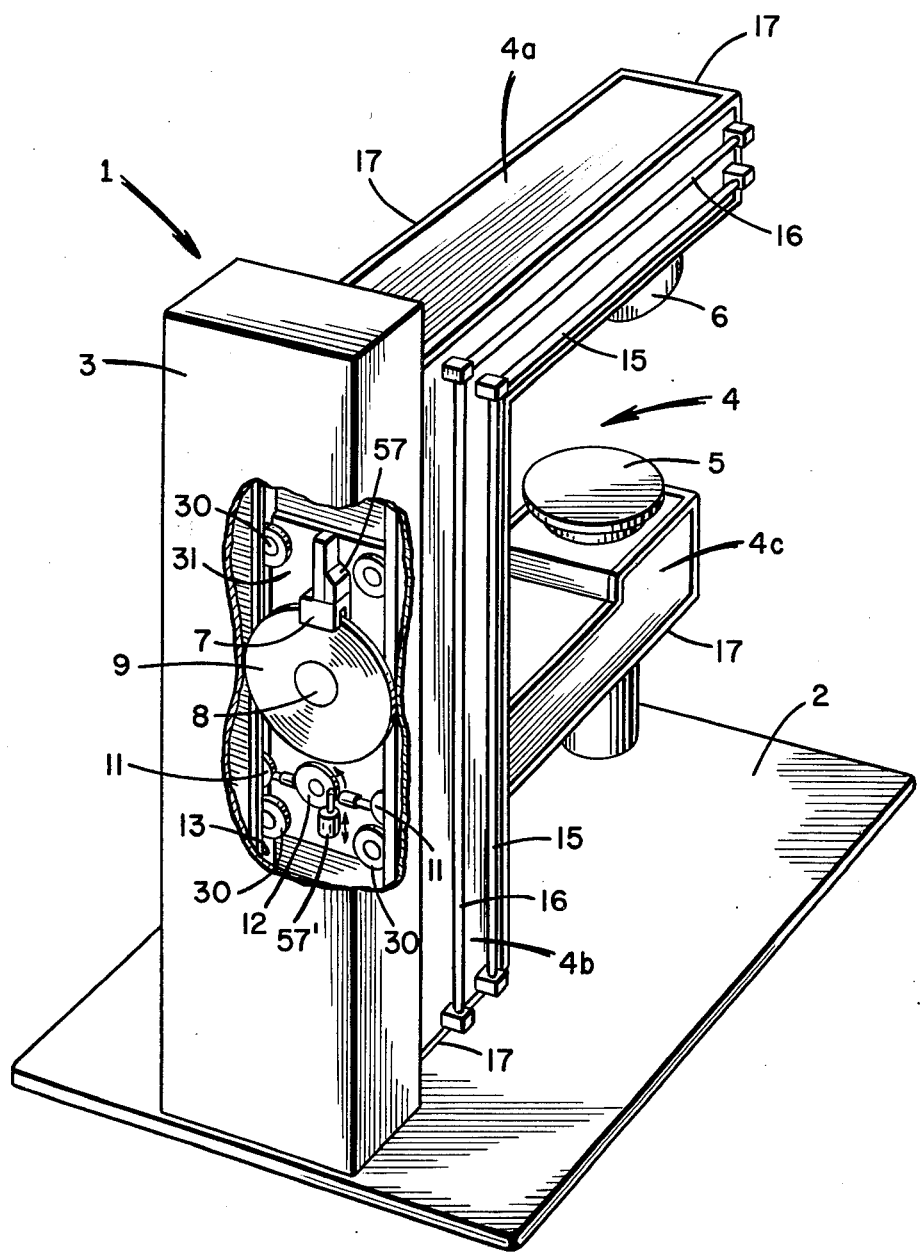
FIG. 1 is a partially sectioned perspective view of a radiography unit stand according to the invention.

A radiography unit stand 1 consists of a baseplate 2 on which a column 3 is disposed. The column 3 can, alternatively, be bolted directly to the floor. A swing arm 4 bearing the radiography equipment 5, 6 is mounted slideably and rotatably in the column. The radiography equipment 5, 6 can be any conventional equipment, such as X-ray equipment well known in the art. Rotary movement of the swing arm is prevented by means of a rotary brake mechanism 7–9. The rotary brake mechanism comprises a caliper 7 which automatically engages a disc 9 by means of a spring mechanism, not shown, to prevent the disc 9 from being rotated. The disc 9 is affixed to a bearing shaft 8 which extends through the column 3 and is attached to the swing arm 4.

The swing arm 4 can also be moved vertically along the column 3, by rollers 30 which are rotatably mounted on a plate 31. The rollers 30 roll along a guide surface 13 within the column 3. A vertical groove 32 is provided in the column 3 to accomodate the bearing shaft 8 as it is moved vertically along the column 3. A vertical brake 11 and 12 is provided comprising a pair of symmetrical brake shoes 11 which are automatically applied against the guide surface 13 by means of a cam 12 which urges the shoes 11 outward against the guide surface 13.

Figure 6:
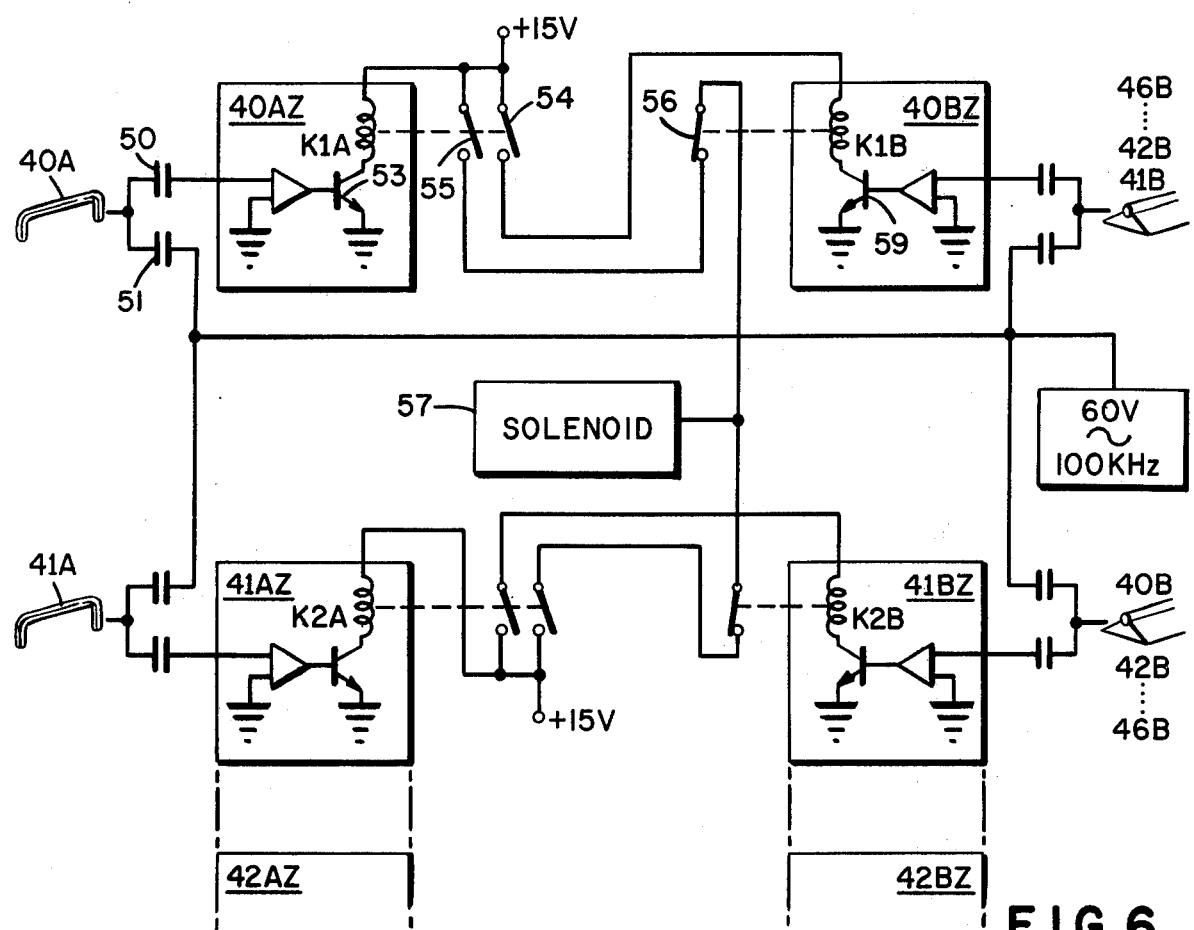
FIG. 6 is a schematic block diagram of the electrical circuitry of the invention.

The rotary brake mechanism 7, 9, is released when an electromagnet or solenoid, shown schematically as numeral 57 in FIGS. 1 and 6, is actuated. The solenoid 57 can be associated with the caliper 7 by electrical wiring, not shown, and when actuated, a solenoid arm, not shown, can release the spring mechanism. Similarly, the solenoid 57', shown schematically in FIG. 1, is provided to rotate the cam 12 in a conventional manner, thus releasing the vertical brake mechanism.

Electrically controlled actuating devices for releasing the brakes can be in the form of handles 15 and 16 extending along the main part of the two angle sections 4a and 4b of the swing arm. When one of the handles, e.g. 15, is held, or touched, the vertical movement brake 13 is released while corresponding actuation of the other handle 16 releases the rotary movement brake 7, in a manner to be described below. The section 4c of the swing arm parallel to the section 4a may also be provided with a handle of the kind indicated although this is not shown in the embodiment illustrated. The other side of the swing arm 4 is also advantageously provided with corresponding handles.

Figure 2:
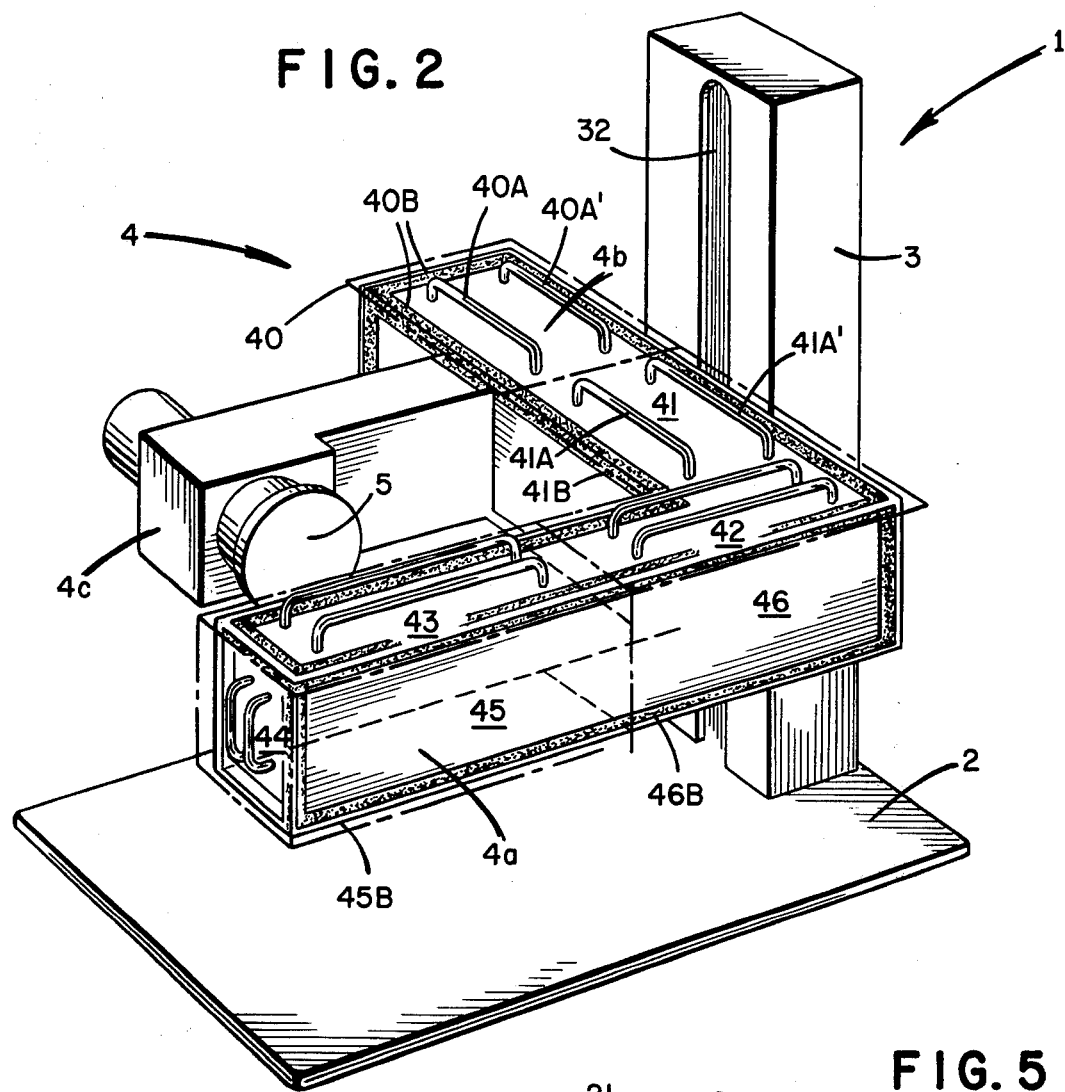
FIG. 2 is a perspective view of an embodiment in which the swing arm is turned 90° relative to the position of the swing arm in FIG. 1.

FIG. 2 shows an alternative embodiment of the apparatus. For convenience, the swing arm 4 is shown to be divided into seven sections, 40–46. Within each section are a pair of actuating devices in the form of short handles 40A, 40A', 41A, 41A', etc. Each of these handles are separately connected with an electrical circuit to be described in detail below, which provide for the release of the rotary and vertical brakes when touched by an operator. One handle within each set is connected to the vertical brake release mechanism, such as 40A, 41A, etc., and the other handle within each set is connected to electrical circuitry which provides for release of the rotary brake mechanism, 40A', 41A', etc. While no handles are shown in sections 45 and 46, it should be appreciated that handles can be provided in those sections. Further handles can be provided along swing arm portion 4c, but are not shown in the drawings. The invention is not limited to any particular number of handles, and it should be recognized that the greater the number of handles mounted on the swing arm, the easier the access to these handles by an operator.

Positioned along the edges of the swing arm 4 shown in FIG. 1, are a plurality of blocking elements 17. These blocking elements comprise metal strips 17 which, when connected with the electrical circuitry to be described below, provide an electromagnetic field of adjustable sensitivity such that when an object, or hand, touch, or approach closely to the metal strip 17, the change in the electrical field that results from the increased capacitance of the object de-activates the brake release circuits, and hence will prevent the releasing of the brake by the actuating device handles. Referring to FIG. 2, these strips are designated as 40B, 41B, etc., and are separate strips for each section of the swing arm 4.

The operation of the preferred embodiment, as shown in FIG. 2, will now be described. When the operator desires to move the swing arm 4 in a particular angular or vertical position, the operator will grip, or touch, one of the handles, such as 40A. The touching of this handle adds a capacitance to the electrical circuit connected to the handle, as described below, which in turn provides power to a solenoid which releases the rotary brake caliper 7. The release of the rotary brake thus enables the operator to manually move the swing arm in a rotatable orientation until the desired position is reached. Similarly, the touching of handle 40A', will release the vertical brake mechanism, thus enabling the swing arm 4 to be moved vertically to the desired position. In the event that, during movement, the swing arm approaches too close to either a patient, the floor, or baseplate 2, or any other objects nearby, the object or patient will touch, or come close to touching, one of the blocking strips, such as 45B. When this strip comes too close to a patient, the capacitance of the patient will alter the electromagnetic field by providing an additional capacitance in the circuit, to be described below. The activation of this circuit will remove power to the solenoid which was actuated by the handles 40, thus deactivating the brake release circuit, and in turn, braking the movement of the swing arm. This provides for a system which is simple to operate, with increased safety advantages so that the risk of injury to persons, or damage to objects in the vicinity of the swing arm, or to the swing arm itself, is avoided. Electrical circuitry is so designed such that the blocking cannot occur in a section in which the control handles are touched or actuated. Thus, for example, if handle 40A or 40A' is touched by an operator, blocking strip 40B is deactivated so that the operator's hand will not accidentally disable the brake release mechanism. Similarly, when handle 41A or 41A' is actuated, blocking strip 41B is deactivated.

It should be noted that the actuating device handles, and the blocking elements, can be designed in a plurality of shapes without departing from the scope of the present invention. For example, the edges of the swing arm in FIG. 1 are provided with a metal strip 17. As shown in FIG. 2, the blocking members can comprise a pipe, which is made of metal, fastened along the edges of the swing arm 4 by means of tape or the like.

Figure 3:
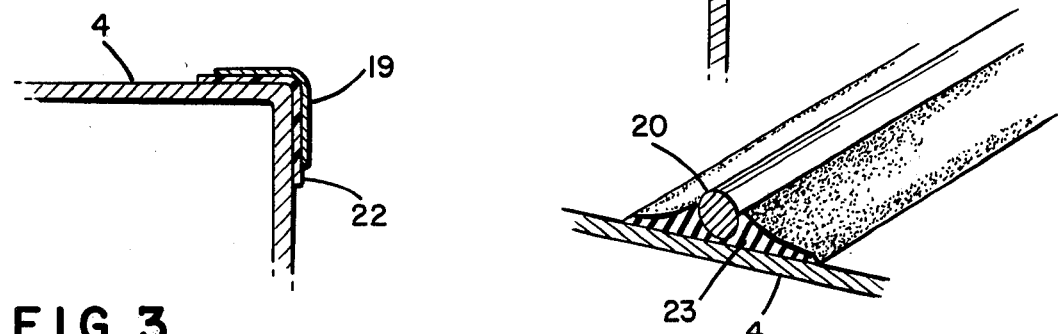
FIG. 3 is a sectioned detail view of an edge of a swing arm, the edge being provided with a blocking element strip which effects a superimposed blocking function for preventing the swing arm movement.

FIG. 3 illustrates another example of how the blocking element can be designed. The edges of the swing arm 4 are provided with an insulated strip 22 made from, for example, plastic to which is attached a bent strip or sheet 19 made from a thin metal, such as copper.

Figure 5:
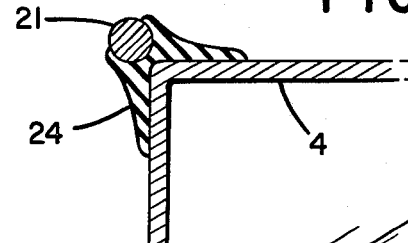
FIG. 5 is a sectioned view of a modification of FIG. 4.
Figure 4:
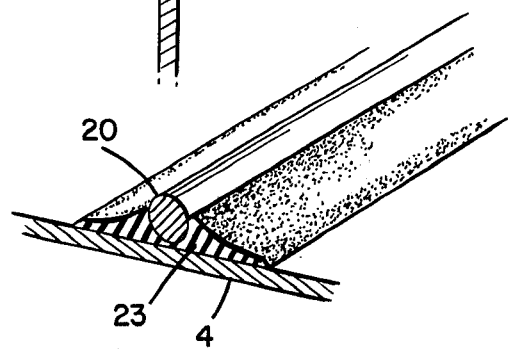
FIG. 4 is a perspective view illustrating a portion of a further swing arm carrying a metal rib as a blocking element.

In the embodiments shown in FIGS. 4 and 5, the blocking elements take the shape of ornamental ribs 20 and 21, on the swing arm. They are made from a suitable metal such a chromium. The rib 20 of FIG. 4 is received in a profiled rubber rim 23, and rib 21 of FIG. 5 is received in a profiled rubber rim 24 having two legs or flanges at right angles to each other and extending along the edges of the swing arm. It should also be recognized that the actuating device handles can be designed in a similar fashion.

The blocking elements and the handle actuating devices are electrical conductors which are electrically connected by wires, not shown, to the electrical circuitry.

Referring now to the electrical circuitry, reference should be made to the block diagram shown in FIG. 6. Handle 40A is connected to a pair of capacitors 50, 51 to which a 60 volt, 100 KHz power source is provided. Capacitor 50 is connected to block 40 AZ, which will be described in detail below. When the handle 40A is touched by an operator, the transistor 53 is turned on, thus providing a circuit path for the 15 volt power source through the coil K1A. Activation of the coil, closes the contacts indicated by the double switches 54, 55. The closing of switch 55 completes the circuit from the 15 volts source through normally closed switch 56 and to the solenoid 57. This solenoid 57 releases one of the brakes, vertical, or rotary. A separate circuit can be provided for the other brake using the handle 40A'. The handles 41A, etc., are operated in a similar manner.

The blocking device 40B is shown connected to a pair of capacitors in a similar manner as the circuit for handle 40A. When, however, handle 40A is touched, blocking element 40B is disabled. That is, blocking element 40B will not actuate the coil K2B, when it is touched, since no power source is provided in this circuit. Thus, blocking element 40B cannot release the solenoid 57. However, reference should be made to blocking elements 41B, 42B, etc., which are shown to be connected in parallel to block 40 BZ through a pair of capacitors. When handle 40A is touched, thus resulting in the closure of switch 54, power is also provided to the coil K1B. Thus, when any of the blocking elements 41B–46B are touched, or come close to a patient or an object, the transistor 59 is turned on, thus completing a circuit through coil K1B. This opens normally closed contact 56 which removes the power to the solenoid 57, thus activating the brake. Similar circuits are provided for the remaining blocking elements.

Figure 7:
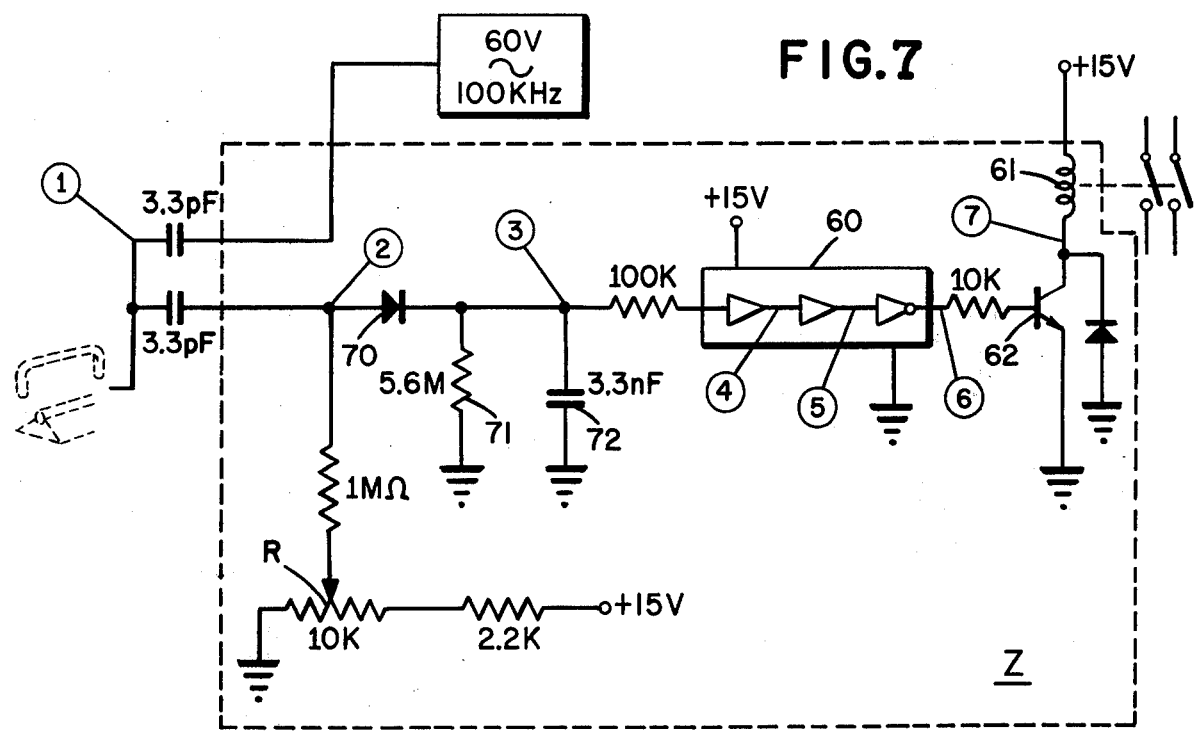
FIG. 7 is a circuit diagram of a portion of the circuit of FIG. 6.

FIG. 7 shows a detailed circuit diagram of the blocks shown in FIG. 6. Since each of these blocks are electrically similar, only one such block Z is shown in FIG. 7. Either a handle, or a blocking strip is connected to a pair of capacitors having a value of 3.3pF. One of the capacitors is connected to a 60 volt, 100 KHZ power source. When the handle or blocking is touched by an object or a person, the additional capacitances caused by the interfering object alters the electrical field characteristics of the circuit. The sensitivity of the circuit can be adjusted by the variable resistor R. When a blocking strip is connected, it is desirable to adjust the resistor R in a manner to increase the sensitivy of the circuit. That is, a smaller amount of capacitance is required to actuate the circuit. Thus, the circuit can be actuated, i.e., the coil 61 can be actuated, when a person or object come close to the blocking strip, without actually contacting the strip. This provides added safety.

Figure 8:
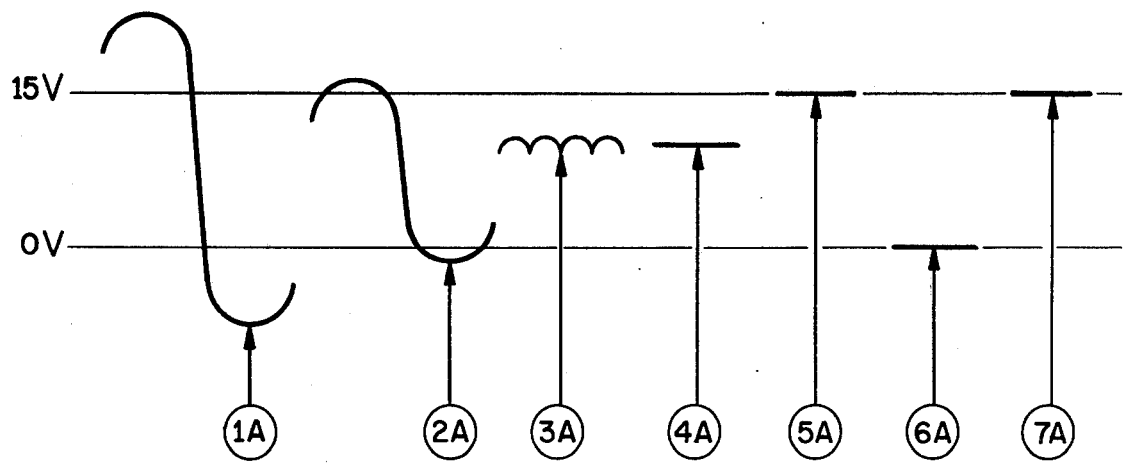
FIG. 8 is a diagram of the various signal waveforms in the circuit of FIG. 7 when the device is not actuated.
Figure 9:
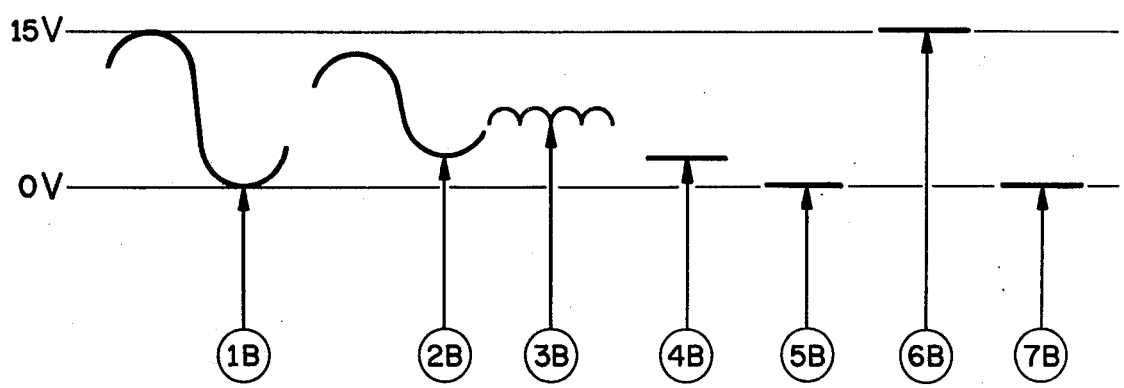
FIG. 9 is a diagram of the various signal waveforms in the circuit of FIG. 8 when the device is actuated.

FIGS. 8 and 9 show the various waveforms in the block Z at the various points designated in FIG. 7. FIG. 8 refers to the waveforms that exist when the device is not actuated, whereas FIG. 9 shows the various waveforms that occur when the handle or blocking element is touched by a person or an object. It should be noted that when the handle or blocking element is touched, thus resulting in additional capacitance in the circuit, the waveform at point 1 of FIG. 7 changes from the waveform 1A in FIG. 8 to the waveform 1B in FIG. 9. The waveform at point 2 in block Z shows the effect of the variable resistor R both in an activated and unactivated state. The waveform at point 3 shows the effect of the diode 70, resistor 71, and capacitor 72, which form a rectifier circuit. Box 60 is a buffer stage which processes the signal as shown at points 4, 5, and 6 of FIGS. 8 and 9. It should be noted that the output stage designated as point 7 in FIG. 7, is at a 15 volt level when a device is not actuated. This corresponds to the transistor 62 being in an open condition. When a device is actuated, by the touching of the handle or blocking element, point 7, as shown in FIG. 7, is at zero volts, which indicates that the transistor is in an "on" position, and current flows therethrough thus activating the coil 61, which in turn actuates the double throw switches as described above.

It should be appreciated to one of ordinary skill in the art that a number of modifications in the device can be provided. For example, if the swing arm unit is large and of great weight, it is often advantageous that the movement of the swing arm, after the brake has been released, be accomplished by an electric motor. In such a case, circuitry can be provided to automatically move the swing arm when the handle is touched.

Further, in some cases, just one handle will be sufficient for actuating both brakes. This can be provided by an alternate form of switch which, when the handle is actuated, one brake mechanism is released, whereupon the next actuation of the handle results in release of the opposite brake. Such alternate types of switches are known in the art.

The figures described herein represent a preferred embodiment of the invention, however other embodiments and numerous modifications are well within the scope of the present invention. These other embodiments and modifications will be apparent to those of ordinary skill in the art.

I claim:

1. A counter-balanced radiography unit stand, comprising a column, a swing arm mounted on said column, radiography means for monitoring patients mounted on said swing arm, means for moving said swing arm vertically and rotatably along the column, automatically applied vertical brake means for preventing the vertical displacement of the swing arm, automatically applied rotary brake means for preventing the rotary movement of the swing arm, electrically controlled actuating means for releasing the vertical and rotary brake means so that the swing arm can be moved rotatably and vertically wherein said actuating means includes contact means disposed along a substantial part of the swing arm length for contact, and electrical circuit means connected to said contact means, whereby the touching of said contact means actuates said electrical circuit means for releasing one of the brake means, wherein said electrical circuit means comprises means for providing an electrical signal to said contact means, means for detecting the touching of said contact means by detecting the change in electrical capacitance caused by touching the contact means, and releasing means for releasing one of the brake means when the contact means is touched.

2. Radiography unit stand according to claim 1, further comprising blocking means for blocking said actuating means to prevent releasing of one of the rotary and vertical brake means when the swing arm approaches or strikes against a person or an object, said blocking means comprising electrically conductive elements positioned on said swing arm and connected to said electrical circuit means for preventing release of one of said brake means when the swing arm approaches or strikes against a person or object.

3. Radiography unit stand according to claim 1 wherein said releasing means comprises a solenoid said solenoid interconnected with one of said brake means, whereby actuation of said solenoid releases one of said brake means.

4. Radiography unit stand according to claim 1 further comprising blocking means for blocking said releasing means, said blocking means comprising electrically conductive elements positioned on said swing arm, said electrical circuit means comprising means for providing an electrical signal to said conductive elements, means for detecting the approach of an object to said conductive elements by detecting the change in electrical capacitance caused by the approach of an object, and disabling means for disabling said releasing means when said conductive elements approach an object.

5. Radiography unit stand according to claim 4 wherein said means for detecting the approach of an object to said conductive elements is adjustable.

* * * * *